United States Patent [19]

Groll et al.

[11] 4,024,144

[45] May 17, 1977

[54] POLYCYCLIC DYESTUFFS

[75] Inventors: Manfred Groll; Volker Hederich, both of Cologne; Hans-Samuel Bien, Burscheid, all of Germany

[73] Assignee: Bayer Aktiengesellschaft, Leverkusen, Germany

[22] Filed: May 19, 1975

[21] Appl. No.: 578,770

[30] Foreign Application Priority Data

May 21, 1974 Germany .................. 2424542

[52] U.S. Cl. ..................... 260/251 A; 260/282
[51] Int. Cl.² ............... C09B 57/00; C07D 487/04; C07D 487/06
[58] Field of Search ................ 260/251 A, 282

[56] References Cited

UNITED STATES PATENTS 3,308,127  3/1967  Senshu ..................... 260/281

FOREIGN PATENTS OR APPLICATIONS 1,550,916  1968  France
457,671   8/1968  Switzerland Primary Examiner—Donald G. Daus
Assistant Examiner—Diana G. Rivers
Attorney, Agent, or Firm—Plumley and Tyner

[57] ABSTRACT

Polycyclic dyestuffs free from sulphonic acid groups of the formula

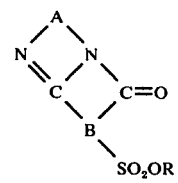

in which
 A denotes an arylene radical and
 B—SO₂—OR denotes an arylene radical substituted by an aryloxysulphonyl group, are suitable for dyeing organic materials, especially for dyeing and printing hydrophobic fibre materials and for bulk-dyeing synthetic materials.

10 Claims, No Drawings

POLYCYCLIC DYESTUFFS

The present invention relates to polycyclic dyestuffs, free from sulphonic acid groups, of the formula

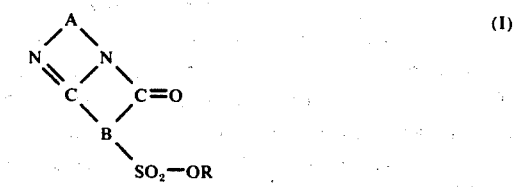

(I)

in which
A denotes an arylene radical and
B—$SO_2OR$ denotes an arylene radical substituted by an aryloxysulphonyl group, as well as to their preparation, and use for dyeing organic materials, especially for dyeing and printing hydrophobic fibre materials and for bulk-dyeing synthetic materials.

Possible arylene radicals A are o-phenylene, o-naphthylene, peri-naphthylene and peri-acenaphthylene radicals which can carry non-ionic substituents.

Possible arylene radicals B are o-phenylene and peri-naphthylene radicals which can also carry non-ionic substituents.

Suitable aryl radicals R are phenyl and naphthyl radicals which can optionally be substituted by $C_1$–$C_8$-alkyl, $C_1$–$C_4$-alkoxy, $C_1$–$C_4$-alkylmercapto, halogeno, nitro, cyano, $C_1$–$C_4$-alkylcarbonylamino, $C_1$–$C_4$-alkoxycarbonyl, $C_1$–$C_4$-alkylcarbonyl, optionally substituted phenyl or phenoxy or which contain fused isocyclic or heterocyclic rings.

The following may be mentioned as examples: phenyl, 2-, 3- or 4-tolyl, 2-ethylphenyl, 4-isopropylphenyl, 4-tert.-butylphenyl, 4-iso-amylphenyl, 4-iso-octylphenyl, 2-, 3- or 4-chlorophenyl, 2,4-dichlorophenyl, 2,6-dichlorophenyl, 3,4-dichlorophenyl, 2,3,4-trichlorophenyl, pentachlorophenyl, 4-bromophenyl, 2-fluorophenyl, 4-nitrophenyl, 3-cyanophenyl, 2-, 3- or 4-trifluoromethylphenyl, 2-, 3- or 4-methoxyphenyl, 2-ethoxyphenyl, 2-isopropoxyphenyl, 4-methylmercaptophenyl, 2-acetylphenyl, 4-acetylphenyl, 4-acetylaminophenyl, 4-methoxycarbonylphenyl, 4-ethoxycarbonylphenyl, 4-propoxycarbonylphenyl, 4-butoxycarbonylphenyl, 2-chloro-5-methylphenyl, biphenylyl, 2- or 4-phenoxyphenyl, α-naphthyl, β-naphthyl, 4- or 3-(diphenylene oxide)-yl, 2- or 3-carbazolyl, 3,4-dioxymethylenephenyl, 2,2-dimethylcoumaranyl-(7), 8-acetylaminonaphthyl-(2), 8-methanesulphonylaminonaphthyl-(2), 3,5-dichloro-4-methoxyphenyl and 3,5-dichloro-2-methoxyphenyl.

Possible non-ionic substituents in A and B are all substituents which are customary in dyestuff chemistry and do not dissociate in an aqueous medium, but especially halogen, such as chlorine and bromine, $C_1$–$C_4$-alkyl groups, $C_1$–$C_4$-alkoxy groups, nitro groups or phenyl groups.

Preferred dyestuffs within the scope of the formula I are those of the formula

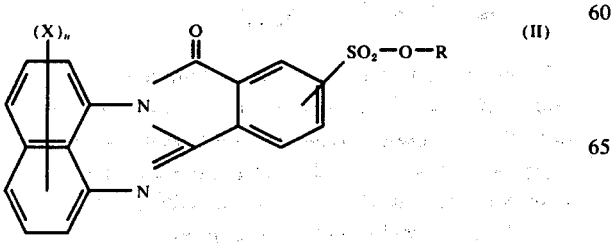

(II)

in which
R has the indicated meaning,
X represents halogen, $C_1$–$C_4$-alkyl or $C_1$–$C_4$-alkoxy and
n represents a number from 0 to 2,
as well as those of the formula

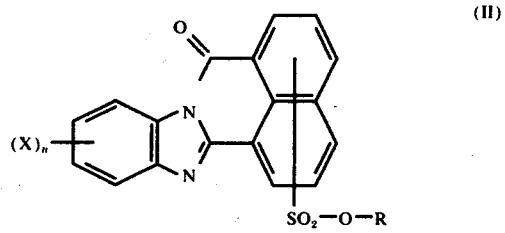

(II)

in which
R, X and n have the indicated meaning, and finally those of the formula

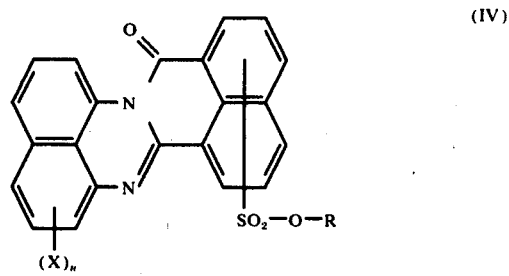

(IV)

in which
R, X and n have the indicated meaning.

A particularly preferred embodiment of the dyestuffs according to the invention corresponds to the isomeric formulae

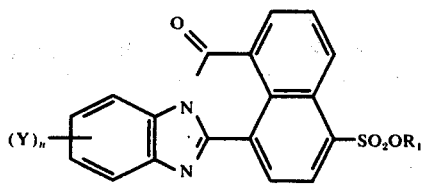

and

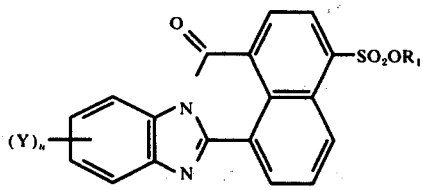

(V)

as well as

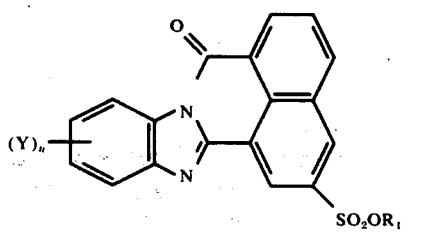

-continued and

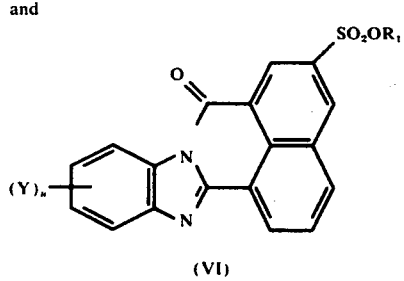

(VI)

in which

R₁ denotes phenyl optionally substituted by chlorine, $C_1$-$C_4$-alkyl or $C_1$-$C_4$-alkoxy, Y denotes $C_1$-$C_4$-alkoxy and n denotes 0 or 1.

The new dyestuffs of the formula (I) are obtained by reacting aromatic dicarboxylic acids or their anhydrides, of the formula

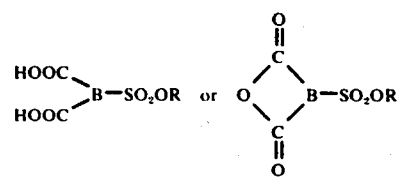

(VII)

in which

B and R have the indicated meaning with aromatic diamines of the formula

(VIII)

in which

A has the indicated meaning or by esterifying polycyclic compounds containing sulphonic acid groups, of the formula

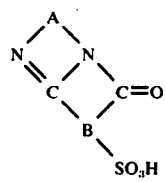

(IX)

in which

A and B have the indicated meaning, via the acid chlorides, by reaction with compounds of the formula

ROH (X)

wherein

R has the indicated meaning.

The non-ionic substituents in A and B can, on their part, either already be present in the starting materials VII–IX or be introduced subsequently.

Thus, for example, halogen atoms can be introduced in accordance with processes which are in themselves known, say in accordance with the instructions in Beilsteins Handbuch der organischen Chemie (Beilstein's Handbook of Organic Chemistry), 24, page 233.

The condensation of the aromatic dicarboxylic acids or their anhydrides (VII) with the aromatic diamines (VIII) is carried out in accordance with methods which are in themselves known, for example in accordance with the instructions of Belgian Pat. Specification 706,794 or German Offenlegungsschrift (German Published Specification) 1,910,586. The condensation is suitably carried out in the presence of an organic solvent which is inert under the reaction conditions.

Examples of suitable solvents are: acetic acid, propionic acid, dimethyltormamide, dimethylacetamide, N-methylpyrrolidone, dimethylsulphoxide, chlorotoluene, dichlorotoluene, dichlorobenzene, trichlorobenzene, nitrobenzene and others. If aromatic diamines (VIII) which do not carry any further substituents are used, mixtures of pairs of isomeric compounds are obtained after the condensation with the appropriate aryloxysulphonyldicarboxylic acids or their anhydrides VII.

If, for example, o-phenylenediamine is reacted with 3-aryloxysulphonylnaphthalic anhydride, the two possible isomers are obtained in accordance with the following equation:

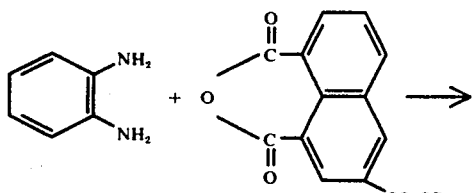

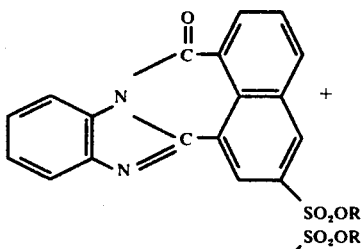

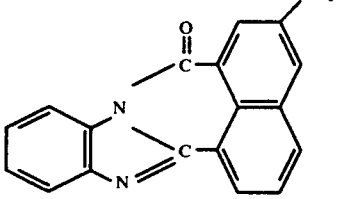

If, on the other hand, aromatic diamines of the formula (VIII) which carry a non-ionic substituent in the radical A are used, mixtures of 4 isomeric compounds are presumably obtained after condensation with the aromatic dicarboxylic acids or anhydrides (VII), in accordance with the following equation:

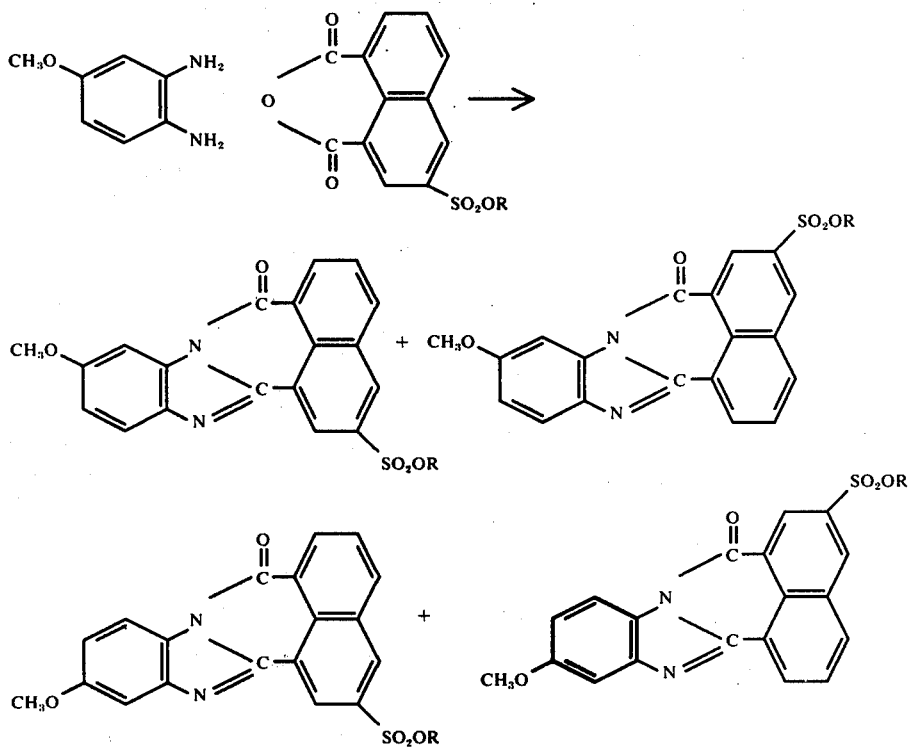

In carrying out this condensation in practice, the procedure followed is preferably that the reactants VII and VIII are reacted in the molar ratio of 1:1, in one of the abovementioned high-boiling organic solvents, at temperatures above 50° C, preferably 100°–150° C.

However, it is also possible to fuse the starting materials together, without using a solvent, in the molar ratio of 1:1, at temperatures of 150°–250° C, preferably 180°–200° C, and in this way to obtain the compounds (I) according to the invention.

Examples of suitable starting materials of the formula (VII) are 4-phenoxysulphonylphthalic acid, 3-phenoxysulphonylphthalic acid, 4-(4-methylphenoxysulphonyl)-phthalic acid, 3-(3-methylphenoxysulphonyl)-phthalic acid, 4-(2-methylphenoxysulphonyl)-phthalic acid, 4-(4-tert.-butylphenoxysulphonyl)-phthalic acid, 4-(4-chlorophenoxysulphonyl)-phthalic acid, 4-(3-chlorophenoxysulphonyl)-phthalic acid, 4-(2-chlorophenoxysulphonyl)-phthalic acid, 4-(4-fluorophenoxysulphonyl)-phthalic acid, 4-(4-bromophenoxysulphonyl)-phthalic acid, 4-(4-nitrophenoxysulphonyl)-phthalic acid, 4-(3-nitrophenoxysulphonyl)-phthalic acid, 4-(3,4-dichlorophenoxysulphonyl)-phthalic acid, 4-(4-methyl-3-nitrophenoxysulphonyl)-phthalic acid, 4-(4-methoxyphenoxysulphonyl)-phthalic acid, 3-(4-methoxyphenoxysulphonyl)-phthalic acid, 4-(3-methoxyphenoxysulphonyl)-phthalic acid, 4-(4-ethoxyphenoxysulphonyl)-phthalic acid, 4-(3-butoxyphenoxysulphonyl)-phthalic acid, 4-(4-methylmercaptophenoxysulphonyl)-phthalic acid, 4-(3-methyl-4-methylmercaptophenoxysulphonyl)-phthalic acid, 4-(4-phenylphenoxy-sulphonyl)-phthalic acid, 4-(4-phenoxyphenoxysulphonyl)-phthalic acid, 4-(α-naphthoxysulphonyl)-phthalic acid, 4-(β-naphthoxysulphonyl)-phthalic acid, 4-[(diphenylene oxide)-3- oxysulphonyl]-phthalic acid, 4-(2,2-dimethylcoumaran-7-oxysulphonyl)-phthalic acid, 4-(8-acetylaminonaphthoxy-2-sulphonyl)-phthalic acid, 4-(3,5-dichloro-4-methoxyphenoxysulphonyl)-phthalic acid and their anhydrides.

Further suitable starting materials of the formula (VII) are 3- or 4-phenoxysulphonyl-1,8-naphthalene-dicarboxylic acid, 3- or 4-(2-methylphenoxysulphonyl)-1,8-naphthalene-dicarboxylic acid, 3- or 4-(3-methylphenoxysulphonyl)-1,8-naphthalene-dicarboxylic acid, 3- or 4-(4-methylphenoxysulphonyl)-1,8-naphthalene-dicarboxylic acid, 3- or 4-(4-ethylphenoxysulphonyl)-1,8-naphthalene-dicarboxylic acid, 3- or 4-(4-isopropylphenoxysulphonyl)-1,8-naphthalene-dicarboxylic acid, 3- or 4-(4-tert.butylphenoxysulphonyl-1,8-naphthalene-dicarboxylic acid, 3- or 4-(2,4-dimethylphenoxysulphonyl)-1,8-naphthalene-dicarboxylic acid, 3- or 4-(2-chlorophenoxysulphonyl-1,8-naphthalene-dicarboxylic acid, 3- or 4-(3-chlorophenoxysulphonyl)-1,8-naphthalene-dicarboxylic acid, 3- or 4-(4-chlorophenoxysulphonyl)-1,8-naphthalene-dicarboxylic acid, 3- or 4-(4-fluorophenoxysulphonyl)-1,8-naphthalene-dicarboxylic acid, 3- or 4-(4-bromophenoxysulphonyl)-1,8-naphthalene-dicarboxylic acid, 3- or 4-(3-nitrophenoxysulphonyl)-1,8-naphthalene-dicarboxylic acid, 3- or 4-(4-nitrophenoxysulphonyl)-1,8-naphthalene-dicarboxylic acid, 3- or 4-(3,4-dichlorophenoxysulphonyl-1,8-naphthalene-dicarboxylic acid, 3- or 4-(2,5-dichlorophenoxysulphonyl)-1,8-naphthalene-dicarboxylic acid, 3- or 4-(2-methyl-5-chlorophenoxysulphonyl)-1,8-naphthalene-dicarboxylic acid, 3- or 4-(2-methoxyphenoxysulphonyl)-1,8-naphthalene-dicarboxylic acid, 3- or 4-(3-methoxyphenoxysulphonyl)-1,8-naphthalene-dicarboxylic acid, 3-or 4-(4-methoxyphenoxysulphonyl)-1,8-naphthalene-dicarboxylic acid, 3- or 4-(2-ethoxyphenoxysulphonyl)-1,8-naphthalene-dicarboxylic acid, 3- or 4-(2-isopropoxyphenoxysulphonyl)-1,8-naphthalene-dicarboxylic acid, 3- or 4-(4-methylmercaptophenoxysulphonyl)-1,8-naphthalene-dicarboxylic acid, 3- or 4-(4- methylsulphonylphenoxysulphonyl)-1,8-naphthalene-dicarboxylic acid, 3- or 4-(4-phenylphenoxysulphonyl)-1,8-naphthalene-dicarboxylic acid, 3- or 4-(4-phenoxyphenoxysulphonyl)-1,8-naphthalene-dicarboxylic acid, 3- or 4-(α-naphthoxysulphonyl)-1,8-naphthalene-dicarboxylic acid, 3- or 4-(β-naphthoxysulphonyl)-1,8-naphthalene-dicarboxylic acid, 3- or 4-[(diphenylene oxide)-3-oxysulphonyl]-1,8-naphthalene-dicarboxylic acid, 3- or 4-(carbazol-3-oxysulphonyl)-1,8-naphthalene-dicarboxylic acid, 3- or 4-(3-hydroxyethoxyphenoxysulphonyl)-1,8-naphthalene-dicarboxylic acid and 3- or 4-(3,4-dioxymethylenephenoxysulphonyl)-1,8-naphthalene-dicarboxylic acid.

Examples of suitable aromatic diamines of the formula (VIII) are: o-phenylenediamine, chloro-o-phenylenediamine, dichloro-o-phenylenediamine, nitro-o-phenylenediamine, methyl-o-phenylenediamine, ethyl-o-phenylenediamine, methoxy-o-phenylenediamine, ethoxy-o-phenylenediamine, acetamino-o-phenylenediamine, dimethyl-o-phenylenediamine, bromo-o-phenylenediamine, trifluoromethyl-o-phenylenediamine, phenyl-o-phenylenediamine and o-naphthylenediamine.

Further suitable aromatic diamines of the formula (VIII) are: 1,8-naphthylenediamine, chloro-1,8-naphthylenediamines, dichloro-1,8-naphthylenediamines, bromo-1,8-naphthylenediamines, methyl-1,8-naphthylenediamines, dimethyl-1,8-naphthylenediamine, methyl-chloro-1,8-naphthylenediamines, methoxy-1,8-naphthylenediamines, ethoxy-1,8-naphthylenediamines, acetamino-1,8-naphthylenediamines, nitro-1,8-naphthylenediamines and 1,8-diaminoacenaphthene.

The new dyestuffs of the formula (I), optionally also as mixtures with one another, are outstandingly suitable for dyeing organic materials, especially for dyeing and/or printing fibers, filaments, woven fabrics, knitted fabrics, tapes, films or sheets of synthetic origin, but above all for dyeing and printing hydrophobic fibre materials. They are dyed or printed in accordance with the methods customary for the fibres. Cellulose triacetate fibres and polyamide fibres can be dyed at about 100° C from aqueous liquors, if appropriate in the presence of the customary auxiliaries. When dyeing fibres of aromatic polyesters, for example polyethylene glycol terephthalate, the customary carriers can be added to the dye bath, or the dyeing can be carried out without added carriers at 120° – ° C under pressure. The dyeings can also be fixed by a brief heat treatment at 190° – 220° C. It is advantageous if, before use, the dyestuffs are brought to a finely divided state in accordance with the customary methods, for example by grinding or kneading, preferably in the presence of customary dispersing agents.

Some types of the dyestuffs according to the invention are furthermore suitable for dyeing synthetic fibre materials from organic solvents in accordance with the so-called continuous process.

The suitable dyeing conditions for this purpose are known and have been described in more detail, for example, in Belgian Patent Specification 753,315. It is frequently advisable to use mixtures of the dyestuffs according to the invention in place of the individual dyestuffs.

Using the abovementioned processes, the dyestuffs of the formula (I) give strong yellow, orange and scarlet dyeings with good fastness properties, especially good fastness to light and to sublimation, on the fibres mentioned.

The dyestuffs of the formula (I) are very particularly suitable for the bulk dyeing of plastics, such as polycarbonates, polymethacrylates, polyamides, polyolefines, polystyrene and, especially, linear synthetic polyesters. By bulk dyeing there is here understood the addition of the dyestuffs before, during or after polymerisation, but before the final shaping process.

For this purpose, the dyestuffs mentioned are used in a finely divided form, and in general no dispersing agents are co-used. The dyestuffs are either obtained in a finely divided form directly during their preparation or are converted to such a form by known, suitable processes, such as by grinding in a dry or moist form, optionally together with organic solvents, or by kneading or grinding the crude product in the presence of solid grinding auxiliaries, such as sodium sulphate, sodium chloride or other salts, which can be eluted after the grinding process. Other methods of obtaining the pigments in a finely divided form are first to dissolve the crude product in sulphuric acid and then reprecipitate it, or to treat it with organic solvents.

The dyestuffs are dry-blended or ground with the plastics granules and this mixture is plasticised and homogenised, for example on mixing rolls or in screws. It is also possible to add the dyestuffs to the molten mass and distribute them homogeneously by stirring. The material predyed in this way is then converted further in the customary manner, for example by spinning to give bristles, filaments and the like, or by extrusion, or by the injection-moulding process, to give mouldings.

It is also possible to add the dyestuffs to the monomeric starting materials for the plastics and then to carry out the polymerisation in the presence of polymerisation catalysts. For this purpose it is on the one hand necessary to dissolve the dyestuffs in the monomeric components or mix them intimately with the monomeric components, whilst on the other hand, the dyestuffs must withstand the action of the polymerisation catalysts.

The polycyclic dyestuffs corresponding to the formula (I) are employed for dyeing the plastics mentioned in proportions of 0.005 to 1%, preferably 0.05 to 0.5%, based on the amount of plastic.

Mouldings of any desired shape, in deep yellow, orange, scarlet and red shades of good fastness properties, especially fastness to light, rubbing, sublimation and washing, are obtained.

EXAMPLE 1

35.4 g of naphthalic anhydride-3-sulphonic acid phenyl ester, or 37.2 g of naphthalic acid-3-sulphonic acid phenyl ester (prepared by treating naphthalic anhydride with chlorosulphonic acid and thionyl chloride and reacting the sulphonic acid chloride with sodium phenolate) are introduced into a solution of 16.7 g of 3,4-diaminophenetole in 48.5 g of o-dichlorobenzene whilst raising the temperature to 60° C, and the mixture is heated to 100°–105° C. It is maintained at this temperature, whilst stirring, until the water produced in the reaction has been distilled off completely. It is then diluted with 200 ml of methanol whilst being cooled, and stirred at room temperature until crystallisation has been completed, and the reaction product is filtered off, washed with methanol and dried.

42.5 g of a yellow dyestuff are thus obtained; this product consists of the dyestuff of the formula

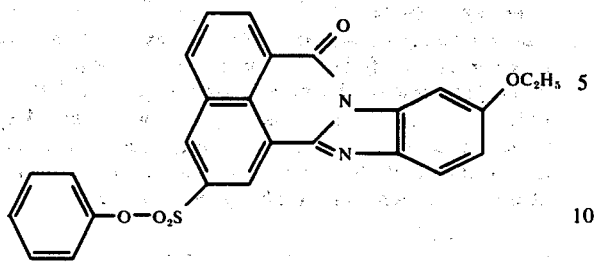
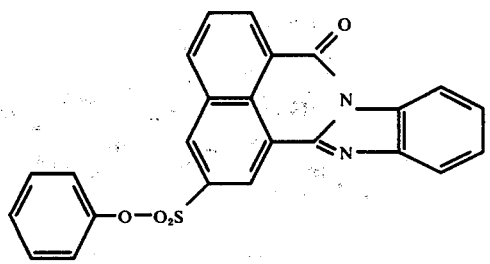

and its positional isomers with regard to the sulphonic acid phenol ester group and ethoxy group.

29.7 g of a paste, moist with water, of naphthalic anhydride-3-sulphonic acid chloride (obtained by treating naphthalic anhydride with chlorosulphonic acid and thionyl chloride at 100° or 85° – 90° C) are introduced slowly into a suspension of 16 g of sodium phenolate in 100 ml of o-dichlorobenzene at 10° – 20° C. The mixture is further stirred for about 2 hours at 20° – 25° C and the water contained in the reaction mixture is distilled off in vacuo together with about 50 ml of o-dichlorobenzene. 17 g of 3,4-diaminophenetole are introduced into the reaction. The temperature is raised to 100° – 105° C and maintained until the condensation has ended. The mixture is cooled and diluted with methanol and the dyestuff is filtered off, washed with methanol and dried.

A yellow dyestuff is obtained, which corresponds to the isomeric mixture described in the preceding paragraph.

1 g of the dyestuft prepared in accordance with the preceding paragraphs is brought to a finely divided state and mixed, in a drum, with 100 g of polyethylene terephthalate chips until these are uniformly covered. The mixture is spun in accordance with customary processes on an extruder spinning machine at 280° C. The resulting filament is then stretched in the ratio of 1 : 4. A polyester filament dyed a deep clear yellow is obtained. The dyeing is distinguised in particular, by very good fastness to light, washing, thermosetting and solvents.

1 g of the dyestuff obtained in accordance with the first two paragraphs, which has been brought to a finely divided state in the presence of a customary dispersing agent, is dispersed in 4 l of water. 15 g of o-cresotic acid methyl ester, as a carrier, and 100 g of polyester fibres (polyethylene terephthalate) are introduced into this dye bath, which is heated to the boil for 2 hours. A clear yellow dyeing of very good fastness to light and to sublimation is obtained.

EXAMPLE 2

23.5 parts of o-phenylenediamine and 35.4 g of naphthalic anhydride-3 sulphonic acid phenyl ester, or 37.2 g of naphthalic acid-3-sulphonic acid phenyl ester, are stirred into 350 ml of glacial acetic acid. The reaction mixture is heated to the boil and stirred until the condensation has ended. It is then cooled to 15° – 20° C and the dyestuff which has crystallised out is filtered off and washed briefly with glacial acetic acid and then with methanol. After drying, 41.2 g of a greenish-tinged yellow dyestuff, which consists of the dyestuff of the formula and the isomeric sulphonic acid phenyl ester, are obtained.

Analogously to Example 1, the dyestuff described above gives polyester fibres dyed a clear greenish-tinged yellow, both by bulk dyeing or by bath dyeing; the bath dyeing can also be carried out under pressure for 1 hour at 125°-130° C.

EXAMPLE 3

18 g of anhydrous sodium acetate are first introduced into 65 g of o-dichlorobenzene. 24.8 g of 3,4-diaminophenetole dihydrochloride are stirred into this suspension at 50° to 60° C. 35.4 g of naphthalic anhydride-4-sulphonic acid phenyl ester or 37.2 g of naphthalic acid-4-sulphonic acid phenyl ester (prepared by treating naphthalic acid-4-sulphonic acid with chlorosulphonic acid and thionyl chloride at 90° C and reacting the sulphonic acid chloride with sodium phenolate) are then introduced. The reaction mixture is now heated to 100° – 105° C and is stirred at this temperature, whilst distilling off the water produced in the reaction, until the condensation has ended. The mixture is then diluted with 200 ml of methanol whilst being cooled, and is stirred at room temperature until crystallisation is complete, and the reaction product is filtered off, washed with methanol and dried.

45 g of a yellow dyestuff are obtained; the product consists of the dyestuff of the formula

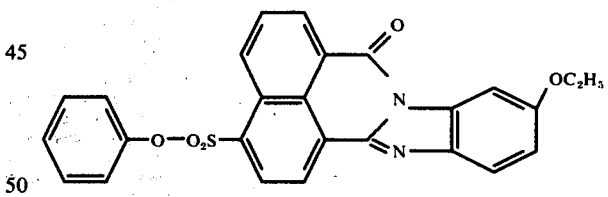

and its positional isomers.

A woven fabric of polyester fibers (polyethylene terephthalate) is impregnated on a padder with a liquor which contains, per liter, 20 g of the dyestuff described above, which has beforehand been brought to a finely divided state in the presence of dispersing agents. Th impregnated fabric is squeezed off to a weight pick-up of 70% and is dried at 100° C. The dyeing is then fixed by treatment with superheated steam at 190° – 220° C for 60 seconds, and is rinsed, washed hot and dried. A brillant reddish-tinged yellow dyeing of very good fastness to light and to sublimation is obtained.

EXAMPLE 4

Analogously to the preparation instructions in Examples 1 to 3, further valuable dyestufts of the following formula

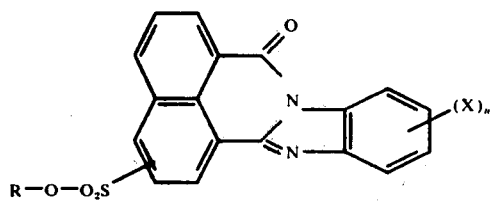

are obtained by reacting corresponding naphthalic acid sulphoaryl esters or their anhydrides with corresponding o-phenylenediamines. The dyestuffs are in each case mixtures of the various possible positional isomers. The table furthermore shows the colour shade on polyester fibres, dyed in accordance with one of the above bulk dyeing or bath dyeing processes, the position of the sulphonic acid ester group and the position of the substituent on the phenylenediamine.

Table 1

| No. | Position of the RO—SO$_2$- group on the naphthalene ring | R | X | Colour shade on polyester |
|---|---|---|---|---|
| 1 | 3 | Phenyl | 4-Chloro | Greenish-tinged yellow |
| 2 | 3 | Phenyl | 4-Nitro | Yellow |
| 3 | 4 | Phenyl | 3-Methyl | Reddish-tinged yellow |
| 4 | 3 | Phenyl | 4-Acetylamino | Reddish-tinged yellow |
| 5 | 3 | Phenyl | 4-Methyl | Greenish-tinged yellow |
| 6 | 4 | Phenyl | 4-Methoxy | Orange yellow |
| 7 | 3 | 2-Tolyl | 3,5-Dimethyl | Greenish-tinged yellow |
| 8 | 3 | 2-Tolyl | 4-Methoxy | Yellow |
| 9 | 3 | 3-Tolyl | 4-Ethoxy | Yellow |
| 10 | 4 | 3-Tolyl | 4-Ethoxy | Orange yellow |
| 11 | 4 | 4-Tolyl | 4-n-Propoxy | Orange yellow |
| 12 | 3 | 4-Tolyl | 4-Methyl | Greenish-tinged yellow |
| 13 | 3 | 2-Ethylphenyl | 4-Chloro | Greenish-tinged yellow |
| 14 | 3 | 4-Isopropylphenyl | 4-Methylmercapto | Yellow |
| 15 | 3 | 4-n-Pentylphenyl | 4-Ethoxy | Yellow |
| 16 | 3 | 2,6-Dimethylphenyl | 4-Methoxy | Yellow |
| 17 | 3 | 3,4-Dimethylphenyl | 4-Methoxy | Yellow |
| 18 | 3 | 4-n-Octylphenyl | 4-Methoxy | Yellow |
| 19 | 3 | 2-Methoxyphenyl | 3-Methyl | Greenish-tinged yellow |
| 20 | 3 | 3-Methoxyphenyl | 3,5-Dimethyl | Greenish-tinged yellow |
| 21 | 3 | 4-Methoxyphenyl | 4-Chloro | Greenish-tinged yellow |
| 22 | 3 | 4-Methylmercaptophenyl | 3-Chloro | Greenish-tinged yellow |
| 23 | 3 | 3-Methyl-4-methylmercaptophenyl | 4-Ethoxy | Yellow |
| 24 | 3 | 4-Ethylmercaptophenyl | 4-Ethoxy | Yellow |
| 25 | 3 | 2-Ethoxyphenyl | 4-Methoxy | Yellow |
| 26 | 4 | 2-Propoxyphenyl | 4-Methoxy | Orange yellow |
| 27 | 3 | 3-Chlorophenyl | 4-Methoxy | Yellow |
| 28 | 3 | 4-Chlorophenyl | 4-Propoxy | Yellow |
| 29 | 3 | 2-Naphthyl | H | Greenish-tinged yellow |
| 30 | 3 | 2-Naphthyl | 4-Methoxy | Yellow |
| 31 | 3 | 2-Naphthyl | 4-Ethoxy | Yellow |
| 32 | 3 | 1-Naphthyl | 3-Chloro | Greenish-tinged yellow |
| 33 | 3 | 1-Naphthyl | 4-Methylmercapto | Yellow |
| 34 | 3 | 1-Naphthyl | 4-Methoxy | Yellow |
| 35 | 3 | 4-Cyclohexylphenyl | H | Greenish-tinged yellow |
| 36 | 4 | 4-Cyclohexylphenyl | 4-Ethoxy | Orange yellow |
| 37 | 4 | 4-Biphenylyl | H | Yellow |
| 38 | 3 | 4-Phenoxyphenyl | 4-Methoxy | Yellow |
| 39 | 4 | 4-Phenoxyphenyl | 4-Chloro | Yellow |
| 40 | 3 | 4-Benzylphenyl | 4-Methoxy | Yellow |
| 41 | 3 | 2-Biphenylyl | 4-Methoxy | Yellow |
| 42 | 3 | 4-(2-Phenylisopropyl)-phenyl | 4-Methoxy | Yellow |
| 43 | 3 | 3,4-Dioxymethylene phenyl | H | Greenish-tinged yellow |
| 44 | 3 | 3-(Diphenylene oxide)-yl | H | Greenish-tinged yellow |
| 45 | 3 | 3-(Diphenylene oxide)-yl | 4-Methylmercapto | Yellow |
| 46 | 3 | 3-(Diphenylene sulphide)-yl | 4-Ethoxy | Yellow |
| 47 | 3 | 3-Carbazolyl | 3-Methyl | Greenish-tinged yellow |
| 48 | 3 | 7-(2,2-Dimethyl-coumaranyl) | 3,5-Dimethyl | Greenish-tinged yellow |
| 49 | 3 | 2-(8-Acetylamino)-naphthyl | 4-Ethoxy | Yellow |
| 50 | 3 | 1-(5-Acetylamino)-naphthyl | 4-Ethoxy | Yellow |
| 51 | 3 | 1-(5-Methanesulphonylamino)-naphthyl | 4-Ethoxy | Yellow |
| 52 | 3 | 4-methylsulphonylphenyl | H | Greenish-tinged yellow |
| 53 | 3 | 4-Methanesulphonyloxyphenyl | H | Greenish-tinged yellow |
| 54 | 3 | 3-Benzenesulphonyloxyphenyl | H | Greenish-tinged yellow |
| 55 | 3 | 4-Methylsulphinylphenyl | H | Greenish-tinged yellow |
| 56 | 3 | 4-Methoxycarbonylphenyl | H | Greenish-tinged yellow |
| 57 | 3 | 4-Ethoxycarbonylphenyl | H | Greenish-tinged yellow |
| 58 | 3 | 4-Propoxycarbonylphenyl | 4-Methoxy | Yellow |
| 59 | 3 | 4-Pentoxycarbonylphenyl | 4-Methoxy | Yellow |
| 60 | 4 | 4-Acetylaminophenyl | 4-Ethoxy | Orange yellow |
| 61 | 4 | 4-Methanesulphonylamino | 4-Ethoxy | Orange yellow |
| 62 | 4 | 3-Acetylaminophenyl | H | Yellow |
| 63 | 3 | 4-Succinimidophenyl | H | Greenish-tinged yellow |
| 64 | 3 | 3-Methyl-4-acetylamino | H | Greenish-tinged yellow |
| 65 | 3 | 4-Anilinophenyl | H | Greenish-tinged yellow |
| 66 | 3 | 4-Trifluoromethylphenyl | H | Greenish-tinged yellow |
| 67 | 3 | 3-Trifluoromethylphenyl | H | Greenish-tinged yellow |
| 68 | 3 | 3,4-Dichlorophenyl | 4,5-Dyclohexeno | Yellow |
| 69 | 3 | 4-Trifluoromethylmercaptophenyl | H | Greenish-tinged yellow |
| 70 | 3 | Phenyl | 3,4-Benzo-5-bromo | Yellow |

Table 1-continued

| No. | Position of the RO—SO₂-group on the naphthalene ring | R | X | Colour shade on polyester |
|---|---|---|---|---|
| 71 | 3 | Phenyl | 3,4-Benzo | Yellow |

EXAMPLE 5

17.3 g of 1,8-naphthylenediamine and 32.8 g of phthalic acid-4-sulphonic acid phenyl ester are stirred into 180 g of 1,2,4-trichlorobenzene. The temperature is raised to 205° – 210° C and the mixture is stirred for some hours, until the condensation has ended, whilst distilling off the water formed in the reaction. The reaction mixture is cooled and slowly diluted with 180 ml of methanol. The dyestuff which has crystallised is filtered off, washed with methanol and dried.

32 g of a red dyestuff are obtained; this product consists of the dyestuff of the formula

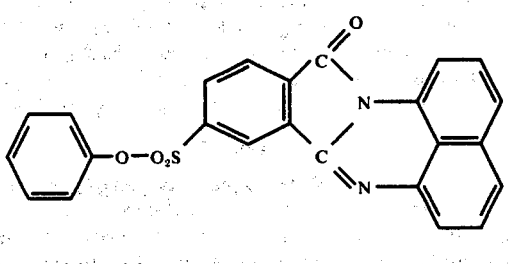

and its positional isomer.

A woven fabric of polyester fibres is impregnated on a padder with a liquor which contains, per litre, 20 g of the dyestuff described above, which has beforehand been brought to a finely divided state in the presence of dispersing agents. The fabic is squeezed off to a weight increase of 70% and dried at 110° C. The dyeing is then fixed by treatment with hot air at 190° – 220° C for 60 seconds, and is rinsed, washed hot and dried. A deep, clear scarlet dyeing having good fastness properties is obtained.

A previously cleaned and heat-set woven fabric of polyethylene terephthalate is printed with a paste consisting of the following components: 20 g of the dyestuff described in the 1st paragraph, in a finely divided form, 520 g of water, 450 g of crystal gum, 1:2, and 10 g of cresotic acid methyl ester. To fix the dyestuff, the printed and dried goods are treated for 40 seconds with hot air at 200° C. After soaping, rinsing and drying, a clear, scarlet-coloured print of good fastness to light and to sublimation is obtained.

EXAMPLE 6

17.3 g of 1,8-diaminonaphthalene and 43.4 g of phthalic acid-4-sulphonic acid 4-isooctylphenyl ester are stirred into 180 g of 1,2,4-trichlorobenzene. The temperature is raised to 205° – 210° C and the mixture is stirred until the condensation has ended, whilst distilling off the water produced in the reaction. The reaction mixture is cooled and the dyestuff is precipitated by adding methanol, filtered off, washed with methanol and dried.

A red dyestuff is obtained in good yield; this product consists of the dyestuff of the formula

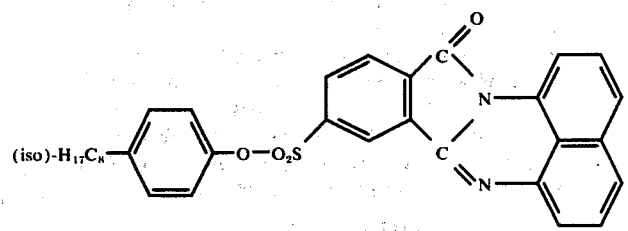

and its positional isomer.

A woven fabric of polyethylene terephthalate fibres is impregnated at room temperature with a clear, red solution which contains 10 g of the dyestuff described above and 990 g of tetrachloroethylene. After squeezing off to a weight increase of 60%, the fabric is dried for 60 seconds at 80° C. It is then heated for 45 seconds to 190° – 220° C to fix the dyestuff. The parts of the dyestuff which have not been fixed are washed out by treating the dyed fabric in cold tetrachloroethylene for 20 seconds. After drying, a clear scarlet dyeing is obtained, which is distinguished by its high dyestuff yield, good build-up and good fastness properties, especially very good fastness to heat-setting, washing, rubbing and light.

Equivalent clear scarlet dyeings are obtained analogously on cellulose triacetate (fixing at 200° – 220° C), synthetic polyamides or polyurethanes (fixing at 170° – 200° C) and polypropylene fibres (fixing at 120° – 150° C).

The tetrachloroethylene used as the solvent can be replaced with equal success by an equal amount of methylene chloride, chloroform, carbon tetrachloride, dichloroethane, trichloroethane, trichloroethylene, 1,1,1-trichloropropane, pentachloropropane, chlorobutane, dichlorobutane, dichlorohexane, 1,2,2-trifluorotrichloroethane, 1,1,1-trifluoropentachloropropane and perfluoro-n-hexane.

EXAMPLE 7

11.5 g of sulphophthaloperinone, prepared from 4-sulphophthalic acid and 1,8-naphthylenediamine in N-methylpyrrolidone, are suspended in 100 ml of xylene. 9.2 g of phosphorus oxychloride are added and the mixture is heated to 80° C for 6 – 7 hours, whilst stirring. 25 – 30 ml of xylene are then distilled off under reduced pressure and after cooling the reaction product which has precipitated is filtered off and the residue is rinsed with petroleum ether. 11.6 g of phthaloperinone-sulphochloride are obtained.

5 g of this sulphochloride are suspended in 60 ml of acetone. 3 g of phenol are added, followed 6 g of triethylamine. The reaction mixture is heated to the boil for 15 minutes, 10 g of glacial acetic acid are then added and the mixture is again boiled for 5 minutes and cooled. The dyestuff is separated out as a solid by adding 100 ml of water. After filtering off and drying, 3.8 g of a dyestuff which is identical with the dyestuff obtained according to Example 5 are obtained.

1 g of this dyestuff is brought to a finely divided state with customary dispersing agents and is suspended in 3 l of water. 100 g of polyester fibres (prepared by polycondensation of terephthalic acid and dimethylolcyclohexane) are added and dyed for one hour at 125° to 130° C under pressure. A strong yellowish-tinged red dyeing of good fastness properties is obtained.

100 g of polyamide woven fabric are dyed for 1 hour at 100° C in 4 l of water with 1 g of the dyestuff prepared in accordance with the second paragraph, which has been brought to a finely divided state. The fabric is then rinsed warm and cold, and dried. A red dyeing of good fastness to washing and to light is obtained.

EXAMPLE 8

Table 2 which follows indicates further valuable dyestuffs and their colour shade on polyester; the dyestuffs are obtained in accordance with the preparation instructions in Examples 5 to 7, from corresponding phthalic acids, or their anhydrides, and corresponding 1,8-naphthylenediamines, or from corresponding phthaloperinone-sulphochlorides and hydroxyaryl compounds. The dyestuffs are again mixtures of the possible positional isomers.

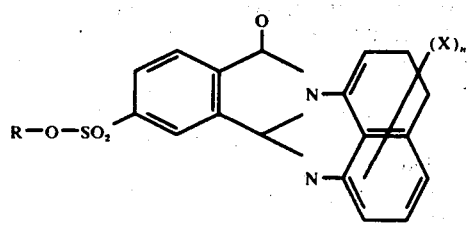

EXAMPLE 9

21 g of crude 3-phenoxysulphonylnaphthalene-dicarboxylic acid anhydride in 150 ml of glacial acetic acid are heated under reflux with 10 g of 1,8-naphthylenediamine for 30 minutes. After cooling, the red dyestuff which has separated out is filtered off and washed with methanol and hot water. 21.5 g of a dyestuff are obtained; this product consists of the dyestuff of the formula

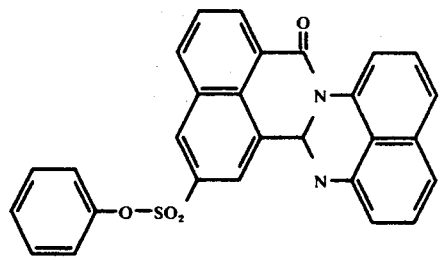

and the compound which is its positional isomer with regard to the phenoxysulphonyl group. A further 3.9 g of the dyestuff are obtained by addition of methanol to the glacial acetic acid filtrate and are purified by recrystallisation from pyridine.

0.1 g of the dyestuff described above are mixed with 100 g of polystyrene granules and the mixture is fused in an extruder at 200° – 220° C. The bulk-dyed polystyrene is then extruded as a ribbon, cooled and granulated. The granulated, dyed polystyrene is injection-moulded on a screw injection moulding machine to give bluish-tinged red mouldings which are distinguished by good fastness to light. The dyestuff shows good heat stability during the processing treatment.

EXAMPLE 10

5 g of the dyestuff prepared according to Example 9 are suspended in 30 ml of o-dichlorobenzene. 4.4 g of bromine dissolved in 10 ml of o-dichlorobenzene are added dropwise over the course of 30 minutes at room temperature. The reaction mixture is stirred for 4 hours at room temperature and the product is filtered off and washed with hot water. 5.4 g of a dyestuff which contains 24.9% by weight of bromine and dyes polystyrene in bluish-tinged red shades are obtained.

Table 2

| No. | R | X | Colour shade on polyester |
|---|---|---|---|
| 1 | 2-Methylphenyl | H | Scarlet |
| 2 | 4-Methylphenyl | H | Scarlet |
| 3 | 4-Chlorophenyl | H | Scarlet |
| 4 | 4-Methoxyphenyl | H | Yellowish-tinged red |
| 5 | 4-Methylmercaptophenyl | H | Yellowish-tinged red |
| 6 | 4-Acetylphenyl | H | Scarlet |
| 7 | 3,4-Dichlorophenyl | H | Scarlet |
| 8 | 2-Chloro-4-methylphenyl | 4-Chloro | Scarlet |
| 9 | 4-Trichloromethylphenyl | 2-Chloro | Scarlet |
| 10 | 4-tert-Butylphenyl | 2-Methyl | Scarlet |
| 11 | 4-Cyclohexylphenyl | H | Scarlet |
| 12 | 4-Biphenylyl | H | Scarlet |
| 13 | 4-Phenoxyphenyl | H | Yellowish-tinged red |
| 14 | 4-Benzylphenyl | H | Scarlet |
| 15 | 2-Isopropoxyphenyl | H | Yellowish-tinged red |
| 16 | 4-Methoxycarbonylphenyl | H | Scarlet |
| 17 | 4-Hydroxyethylphenyl | 4-Chloro | Scarlet |
| 18 | 2-Diphenylene oxide)-yl | 4,5-Ethylene | Yellowish-tinged red |
| 19 | 2-Diphenylene sulphide)-yl | 4,5-Ethylene | Yellowish-tinged red |
| 20 | 3,4-Dioxymethylenephenyl | H | Yellowish-tinged red |
| 21 | 7-(2,2-Dimethylcoumaranyl) | H | Yellowish-tinged red |

EXAMPLE 11

Further valuable dyestuffs which, for example, dye polystyrene in the shades indicated, are indicated in Table 3. The dyestuffs are prepared in accordance with the instructions of Example 9 from corresponding aryloxysulphonylnaphthalic acids or their anhydrides and corresponding 1,8-naphthylenediamines and are mixtures of the various possible positional isomers. Column 1 indicates the substitution position of the aryloxysulphonyl radical on the naphthalic acid system.

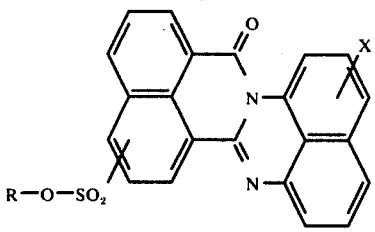

Table 3

| No. | Position of the RO—SO$_2$— group on the naphthalene ring | R | X | Colour shade on polyester |
|---|---|---|---|---|
| 1 | 3 | 4-Chlorophenyl | H | Bluish-tinged red |
| 2 | 4 | 3-Methoxyphenyl | H | Red violet |
| 3 | 3 | 4-Methylmercaptophenyl | H | Bluish-tinged red |
| 4 | 4 | 3,4-Dimethylphenyl | 4-Chloro | Red-violet |
| 5 | 3 | 4-n-Pentylphenyl | 2-Chloro | Bluish-tinged red |
| 6 | 3 | 4-Acetylphenyl | 2-Methyl | Bluish-tinged red |
| 7 | 3 | 4-Sulphamoylphenyl | H | Bluish-tinged red |
| 8 | 3 | 2-Cyclopentyloxyphenyl | H | Bluish-tinged red |
| 9 | 3 | 4-Cyclohexylphenyl | H | Bluish-tinged red |
| 10 | 3 | 4-Phenoxyphenyl | H | Bluish-tinged red |
| 11 | 3 | 3-(Diphenyl oxide)-yl | H | Bluish-tinged red |
| 12 | 3 | 3-Diphenylenesulphidyl | H | Bluish-tinged red |
| 13 | 3 | 1-Naphthyl | H | Bluish-tinged red |

EXAMPLE 12

5 g of the dyestuff prepared according to Example 2 are dissolved in 70 g of 90% strength sulphuric acid. 2 g of boric acid and 0.1 g of iodine are added, 2.6 g of bromine are then added dropwise to the reaction mixture and the whole is stirred for 24 hours at room temperature. The reaction mixture is then poured onto 200 g of ice, the precipitate is filtered off and washed with dilute sodium bisulphite solution and then with water, and after drying 4.8 g of the dyestuff of the formula

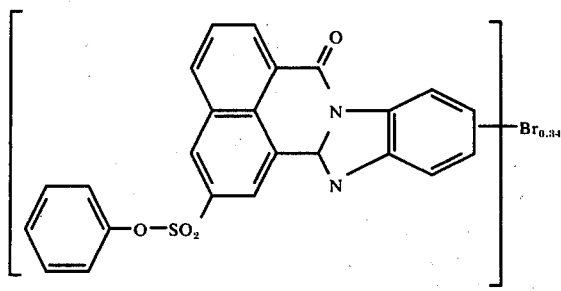

are obtained; this product contains 5.3% of bromine and consists of a mixture of the possible positional isomers.

100 g of cellulose triacetate fibres are introduced into a dye bath which consists of 3 l of water, 1 g of the dyestuff described above, in a finely divided form and 6 g of a fatty alcohol sulphonate, and are dyed for 1 hour at 100° C. A yellow dyeing of good fastness to washing, heat-setting and light is obtained.

EXAMPLE 13

17 g of anhydrous sodium acetate in 75 ml of o-dichlorobenzene are warmed to 50° C. 23 g of 3,4-diaminophenetole dihydrochloride are added thereto, followed, after 10 minutes, by 25.5 g of phthalic acid-4-sulphonic acid phenyl ester. The temperature is raised to 180° C over the course of 1 hour and the mixture is stirred for 2 hours at this temperature. The o-dichlorobenzene is then largely removed in vacuo at about 100° C and the residue is diluted with methanol. After cooling to 20° C, the product is filtered off and briefly washed with methanol. The filter residue is stirred with water and dried. The intermediate product thus obtained is stirred in 100 ml of 1,2,4-trichlorobenzene for 4 hours at 215° C, during which time the water formed in the reaction is distilled off. The mixture is then cooled and diluted with methanol, and the dyestuff obtained as yellow crystals is filtered off, washed with methanol, thoroughly stirred with water and dried. The dyestuff consists of the compound of the formula

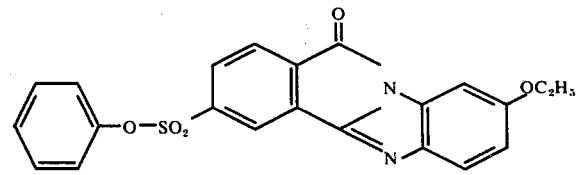

and the corresponding positional isomers.

EXAMPLE 14

8 g of 1,8-naphthylenediamine are introduced into a solution of 21.6 g of 4-bromo-x-phenoxysulphonyl-1,8-naphthalic anhydride (prepared by sulphochlorination of 4-bromophthalic anhydride and esterification with sodium phenolate) in 80 ml of glacial acetic acid. The mixture is heated to the boil for 15 minutes and after cooling the dyestuff which has separated out is filtered off and washed with methanol and hot water. After drying, 24.3 g of a dyestuff are obtained; this product consists of the dyestuff of the formula

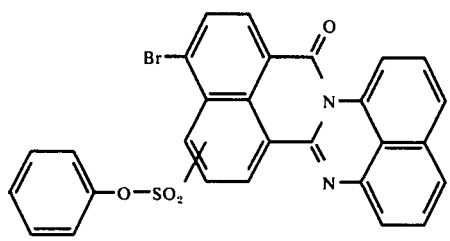

and its positional isomers.

EXAMPLE 15

If, in Example 14, the naphthylenediamine is replaced by 5.6 g of ortho-phenylenediamine, 18.7 g of a yellow dyestuff are obtained; this product consists of the dyestuff of the formula

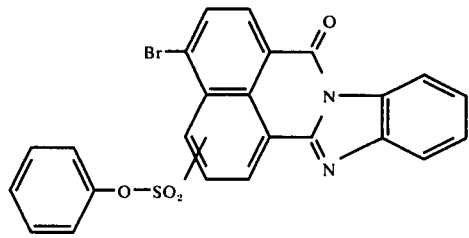

and its positional isomers.

The dyestuff dyes polyester materials in yellow shades having very good fastness properties.

We claim:

1. Polycyclic dyestuff, free from sulphonic acid groups, of the formula

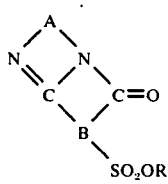

in which
A denotes o-phenylene, o-naphthylene or peri-naphthylene;
B denotes o-phenylene or peri-naphthylene;
A and B are unsubstituted or substituted by chlorine, bromine, $C_1$–$C_4$-alkyl, $C_1$–$C_4$-alkoxy, nitro or phenyl;
R denotes phenyl; naphthyl; phenyl or naphthyl substituted by $C_1$–$C_8$-alkyl, $C_1$–$C_4$-alkoxy, $C_1$–$C_4$-alkylmercapto, halogeno, nitro, cyano, $C_1$–$C_4$-alkylcarbonylamino, $C_1$–$C_4$-alkoxycarbonyl, $C_1$–$C_4$-alkylcarbonyl, phenyl or phenoxy.

2. Polycyclic dyestuffs according to claim 1 of the formulae

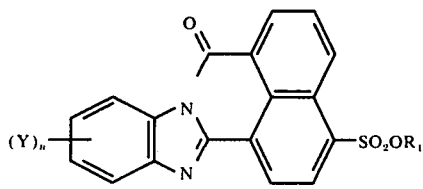

and

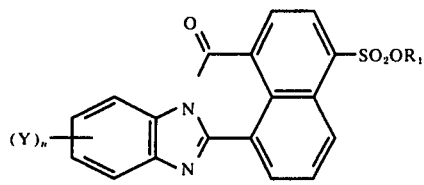

wherein
$R_1$ denotes phenyl; or phenyl substituted by chlorine, $C_1$–$C_4$-alkyl or $C_1$–$C_4$-alkoxy;
Y denotes $C_1$–$C_4$-alkoxy; and
n denotes 0 or 1.

3. Polycyclic dyestuffs according to claim 1 of the formulae

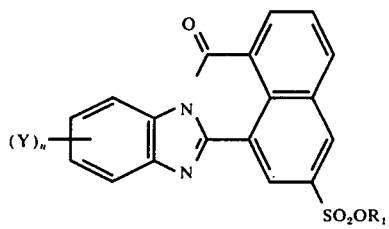

and

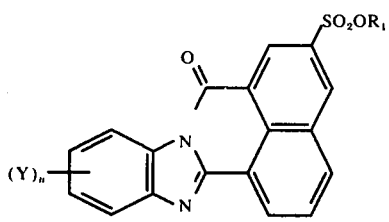

wherein
$R_1$ denotes phenyl; or phenyl substituted by chlorine, $C_1$–$C_4$-alkyl or $C_1$–$C_4$-alkoxy;
Y denotes $C_1$–$C_4$-alkoxy; and
n denotes 0 or 1.

4. Polycyclic dyestuff according to claim 1, of the formula

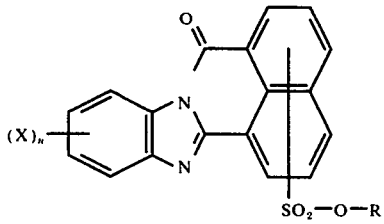

in which
R denotes phenyl; naphthyl; phenyl or naphthyl substituted by $C_1$–$C_8$-alkyl, $C_1$–$C_4$-alkoxy, $C_1$–$C_4$-alkylmercapto, halogeno, nitro, cyano, $C_1$–$C_4$-alkylcarbonylamino, $C_1$–$C_4$-alkoxycarbonylamino, $C_1$–$C_4$-alkoxycarbonyll, phenyl or phenoxy;
X denotes halogen, $C_1$–$C_4$-alkyl or $C_1$–$C_4$-alkoxy; and
n represents a number from 0 to 2.

5. Polycyclic dyestuff according to claim 1 of the formula

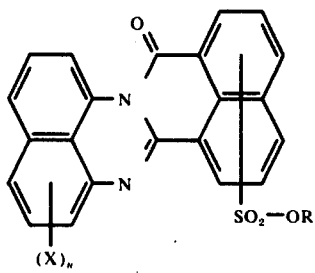

in which

R denotes phenyl; naphthyl; phenyl or naphthyl substituted by $C_1$–$C_8$-alkyl, $C_1$–$C_4$-alkoxy, $C_1$–$C_4$-alkylmercapto, halogeno, nitro, cyano, $C_1$–$C_4$-alkylcarbonylamino, $C_1$–$C_4$-alkoxycarbonylamino, $C_1$–$C_4$-alkoxycarbonyll, phenyl or phenoxy;

X denotes halogen, $C_1$–$C_4$-alkyl or $C_1$–$C_4$-alkoxy; and n represents a number from 0 to 2.

6. The dyestuff of claim 1 of the formula

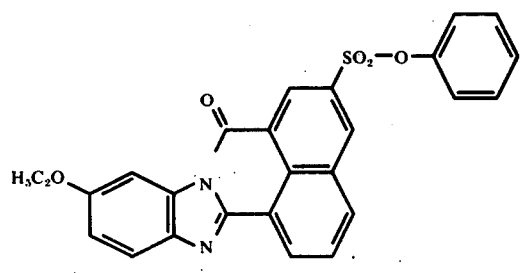

7. The dyestuft of claim 1 of the formula

8. The dyestuff of claim 1 of the formula

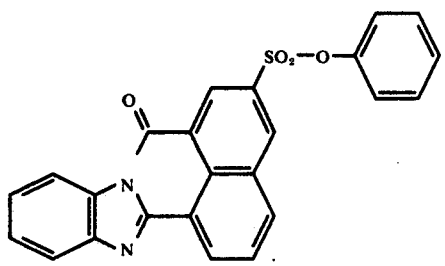

9. The dyestuff of claim 1 of the formula

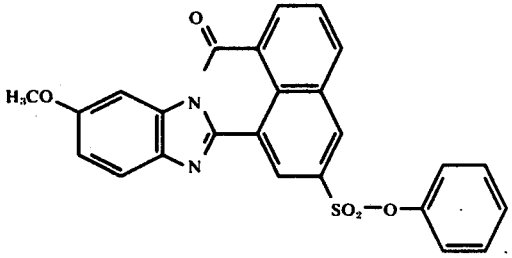

10. The dyestuff of claim 1 of the formula

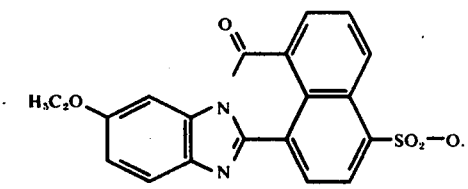

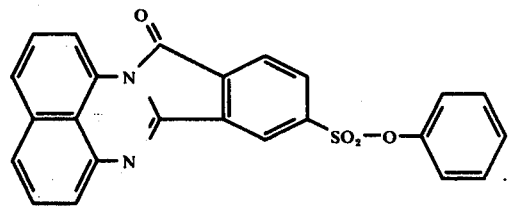

* * * * *